US009387138B2

(12) United States Patent
Roe

(10) Patent No.: US 9,387,138 B2
(45) Date of Patent: Jul. 12, 2016

(54) REUSABLE OUTER COVERS FOR WEARABLE ABSORBENT ARTICLES

(75) Inventor: Donald Carroll Roe, West Chester, OH (US)

(73) Assignee: The Procter & Gamble Company, Cincinnati, OH (US)

(*) Notice: Subject to any disclaimer, the term of this patent is extended or adjusted under 35 U.S.C. 154(b) by 1614 days.

(21) Appl. No.: 12/687,444

(22) Filed: Jan. 14, 2010

(65) Prior Publication Data

US 2010/0179499 A1 Jul. 15, 2010

Related U.S. Application Data

(60) Provisional application No. 61/144,883, filed on Jan. 15, 2009.

(51) Int. Cl.
*A61F 13/505* (2006.01)
*A61F 13/56* (2006.01)
*A61F 13/49* (2006.01)
*A61F 13/15* (2006.01)

(52) U.S. Cl.
CPC ....... *A61F 13/5622* (2013.01); *A61F 13/15268* (2013.01); *A61F 13/49003* (2013.01); *A61F 13/49014* (2013.01); *A61F 13/505* (2013.01); *A61F 2013/15333* (2013.01)

(58) Field of Classification Search
CPC ............ A61F 13/15268; A61F 13/49003; A61F 13/49004; A61F 13/505; A61F 2013/15276; A61F 2013/15325; A61F 2013/15333; A61F 2013/5055

USPC ............ 604/385.14, 385.1, 385.22, 392–396
See application file for complete search history.

(56) References Cited

U.S. PATENT DOCUMENTS

| | | | |
|---|---|---|---|
| 2,119,610 | A | 6/1938 | Robert |
| 2,530,647 | A | 11/1950 | Buchler |
| 2,688,328 | A | 9/1954 | Marcus |
| 2,793,642 | A | 5/1957 | Andruhovici |
| 3,077,193 | A | 2/1963 | Mann |
| 3,496,259 | A | 2/1970 | Guenther |
| 3,560,292 | A | 2/1971 | Butter |
| 3,719,736 | A | 3/1973 | Woodruff |
| 3,735,424 | A | 5/1973 | Maggio et al. |
| 3,860,003 | A | 1/1975 | Buell |
| 3,911,173 | A | 10/1975 | Sprague, Jr. |
| 3,926,189 | A | 12/1975 | Taylor |
| 3,929,135 | A | 12/1975 | Thompson |
| 3,955,575 | A | 5/1976 | Okuda |
| 4,022,210 | A | 5/1977 | Glassman |
| 4,072,150 | A | 2/1978 | Glassman |

(Continued)

FOREIGN PATENT DOCUMENTS

| | | |
|---|---|---|
| AU | 642 386 | 10/1993 |
| CA | 2 103 537 | 2/1995 |

(Continued)

OTHER PUBLICATIONS

International Search Report and Written Opinion, PCT/US2010/021173, date of mailing May 28, 2010.

(Continued)

*Primary Examiner* — Lynne Anderson
(74) *Attorney, Agent, or Firm* — Christian M. Best; Charles R. Ware

(57) ABSTRACT

Reusable outer covers for wearable absorbent articles.

31 Claims, 1 Drawing Sheet

(56) References Cited

U.S. PATENT DOCUMENTS

| | | | |
|---|---|---|---|
| 4,081,301 | A | 3/1978 | Buell |
| 4,116,892 | A | 9/1978 | Schwarz |
| 4,195,634 | A | 4/1980 | DiSalvo et al. |
| 4,223,059 | A | 9/1980 | Schwarz |
| 4,265,245 | A | 5/1981 | Glassman |
| 4,284,454 | A | 8/1981 | Joa |
| 4,324,246 | A | 4/1982 | Mullane et al. |
| 4,326,302 | A | 4/1982 | Lowe et al. |
| 4,338,939 | A | 7/1982 | Daville |
| 4,342,314 | A | 8/1982 | Radel et al. |
| 4,352,356 | A | 10/1982 | Tong |
| 4,438,167 | A | 3/1984 | Schwarz |
| 4,463,045 | A | 7/1984 | Ahr et al. |
| 4,475,912 | A | 10/1984 | Coates |
| 4,496,360 | A | 1/1985 | Joffe et al. |
| 4,573,986 | A | 3/1986 | Minetola et al. |
| 4,578,073 | A | 3/1986 | Dysart et al. |
| 4,579,556 | A | 4/1986 | McFarland |
| 4,582,550 | A | 4/1986 | Sigl |
| 4,597,760 | A | 7/1986 | Buell |
| 4,597,761 | A | 7/1986 | Buell |
| 4,609,518 | A | 9/1986 | Curro et al. |
| 4,610,678 | A | 9/1986 | Weisman et al. |
| 4,615,695 | A | 10/1986 | Cooper |
| 4,625,245 | A | 11/1986 | White |
| 4,629,643 | A | 12/1986 | Curro et al. |
| 4,643,726 | A | 2/1987 | Gegelys |
| 4,650,483 | A | 3/1987 | Joffe |
| 4,657,539 | A | 4/1987 | Hasse |
| 4,661,102 | A | 4/1987 | Shikata et al. |
| 4,673,402 | A | 6/1987 | Weisman et al. |
| 4,695,278 | A | 9/1987 | Lawson |
| 4,701,170 | A | 10/1987 | Wilson et al. |
| 4,704,114 | A | 11/1987 | Wilson et al. |
| 4,704,116 | A | 11/1987 | Enloe |
| 4,710,187 | A | 12/1987 | Boland et al. |
| 4,747,846 | A | 5/1988 | Boland et al. |
| 4,756,709 | A | 7/1988 | Stevens |
| 4,770,656 | A | 9/1988 | Proxmire et al. |
| 4,785,996 | A | 11/1988 | Ziecker et al. |
| 4,795,452 | A | 1/1989 | Blaney et al. |
| 4,795,454 | A | 1/1989 | Dragoo |
| 4,808,176 | A | 2/1989 | Kielpikowski |
| 4,808,177 | A | 2/1989 | Desmarais et al. |
| 4,808,178 | A | 2/1989 | Aziz et al. |
| 4,816,026 | A | 3/1989 | Richardson |
| 4,834,735 | A | 5/1989 | Alemany et al. |
| 4,834,736 | A | 5/1989 | Boland et al. |
| 4,834,737 | A | 5/1989 | Khan |
| 4,834,738 | A | 5/1989 | Kielpikowski et al. |
| 4,842,666 | A | 6/1989 | Werenicz |
| 4,872,871 | A | 10/1989 | Proxmire et al. |
| 4,888,231 | A | 12/1989 | Angstadt |
| 4,892,536 | A | 1/1990 | Desmarais et al. |
| 4,892,598 | A | 1/1990 | Stevens et al. |
| 4,906,243 | A | 3/1990 | Dravland |
| 4,908,247 | A | 3/1990 | Baird et al. |
| 4,909,803 | A | 3/1990 | Aziz et al. |
| 4,955,880 | A | 9/1990 | Rodriquez |
| 4,961,736 | A | 10/1990 | McCloud |
| 4,964,857 | A | 10/1990 | Osborn |
| 4,968,311 | A | 11/1990 | Chickering et al. |
| 4,968,312 | A | 11/1990 | Khan |
| 4,978,046 | A | 12/1990 | Hagmann et al. |
| 4,988,344 | A | 1/1991 | Reising et al. |
| 4,988,345 | A | 1/1991 | Reising |
| 4,990,147 | A | 2/1991 | Freeland |
| 5,006,394 | A | 4/1991 | Baird |
| 5,019,068 | A * | 5/1991 | Perez et al. ............... 604/386 |
| 5,021,051 | A | 6/1991 | Hiuke |
| 5,032,120 | A | 7/1991 | Freeland et al. |
| 5,037,416 | A | 8/1991 | Allen et al. |
| 5,069,672 | A * | 12/1991 | Wippler et al. .......... 604/385.14 |
| 5,087,253 | A | 2/1992 | Cooper |
| 5,108,385 | A | 4/1992 | Snyder |
| 5,127,108 | A | 7/1992 | Weiss |
| 5,137,537 | A | 8/1992 | Herron et al. |
| 5,141,870 | A | 8/1992 | Bedbrook et al. |
| 5,147,345 | A | 9/1992 | Young et al. |
| 5,156,793 | A | 10/1992 | Buell et al. |
| 5,167,897 | A | 12/1992 | Weber et al. |
| 5,185,011 | A | 2/1993 | Strasser |
| 5,202,173 | A | 4/1993 | Wu et al. |
| 5,207,663 | A | 5/1993 | McQueen |
| 5,210,882 | A | 5/1993 | Moretz et al. |
| 5,217,447 | A * | 6/1993 | Gagnon ..................... 604/397 |
| 5,234,423 | A | 8/1993 | Alemany et al. |
| 5,254,111 | A | 10/1993 | Cancio et al. |
| 5,260,345 | A | 11/1993 | Desmarais et al. |
| 5,261,901 | A | 11/1993 | Guay |
| 5,269,775 | A | 12/1993 | Freeland et al. |
| 5,283,910 | A | 2/1994 | Flint |
| 5,290,270 | A | 3/1994 | Fisher |
| 5,296,184 | A | 3/1994 | Wu et al. |
| 5,306,267 | A * | 4/1994 | Hahn et al. .............. 604/378 |
| 5,342,338 | A | 8/1994 | Roe |
| 5,354,597 | A | 10/1994 | Capik et al. |
| 5,360,422 | A * | 11/1994 | Brownlee et al. ........ 604/385.15 |
| 5,368,584 | A | 11/1994 | Clear et al. |
| 5,368,585 | A | 11/1994 | Dokken |
| 5,387,207 | A | 2/1995 | Dyer et al. |
| 5,401,266 | A | 3/1995 | Runeman et al. |
| 5,405,342 | A | 4/1995 | Roessler et al. |
| 5,415,650 | A | 5/1995 | Sigl |
| 5,435,014 | A | 7/1995 | Moretz et al. |
| 5,458,591 | A | 10/1995 | Roessler et al. |
| 5,476,457 | A | 12/1995 | Roessler et al. |
| 5,509,915 | A | 4/1996 | Hanson et al. |
| 5,514,121 | A | 5/1996 | Roe et al. |
| 5,518,801 | A | 5/1996 | Chappell et al. |
| 5,554,142 | A | 9/1996 | Dreier et al. |
| 5,562,648 | A | 10/1996 | Peterson |
| 5,571,096 | A | 11/1996 | Dobrin et al. |
| 5,607,760 | A | 3/1997 | Roe |
| 5,609,587 | A | 3/1997 | Roe |
| 5,613,959 | A | 3/1997 | Roessler et al. |
| 5,624,425 | A | 4/1997 | Gray et al. |
| 5,624,429 | A | 4/1997 | Long et al. |
| 5,625,222 | A | 4/1997 | Yoneda et al. |
| 5,635,191 | A | 6/1997 | Roe et al. |
| H1670 | H | 7/1997 | Aziz et al. |
| 5,643,588 | A | 7/1997 | Roe et al. |
| 5,667,503 | A | 9/1997 | Roe et al. |
| 5,671,615 | A | 9/1997 | Kjærgaard et al. |
| 5,716,349 | A | 2/1998 | Taylor et al. |
| H1732 | H | 6/1998 | Johnson |
| 5,769,838 | A | 6/1998 | Buell et al. |
| 5,772,649 | A | 6/1998 | Siudzinski |
| 5,776,121 | A | 7/1998 | Roe et al. |
| 5,795,347 | A | 8/1998 | Roe et al. |
| 5,795,348 | A | 8/1998 | Roe et al. |
| 5,814,037 | A | 9/1998 | Coates |
| 5,827,261 | A | 10/1998 | Osborn et al. |
| 5,843,065 | A | 12/1998 | Wyant |
| 5,843,267 | A | 12/1998 | Cashaw et al. |
| 5,846,232 | A | 12/1998 | Serbiak et al. |
| H1788 | H | 2/1999 | Christon et al. |
| 5,865,823 | A | 2/1999 | Curro |
| 5,906,603 | A | 5/1999 | Roe et al. |
| 5,911,713 | A | 6/1999 | Yamada et al. |
| 5,938,648 | A | 8/1999 | Lavon et al. |
| 5,941,864 | A | 8/1999 | Roe |
| 5,947,946 | A | 9/1999 | Fisher et al. |
| 5,968,025 | A | 10/1999 | Roe et al. |
| 5,984,911 | A | 11/1999 | Siebers et al. |
| 6,007,528 | A | 12/1999 | Osborn |
| 6,010,491 | A | 1/2000 | Roe et al. |
| 6,120,487 | A | 9/2000 | Ashton |
| 6,142,983 | A | 11/2000 | Suprise et al. |
| 6,207,738 | B1 | 3/2001 | Zuckerman et al. |
| 6,213,991 | B1 | 4/2001 | Kling et al. |
| 6,229,061 | B1 | 5/2001 | Draggo et al. |
| 6,240,569 | B1 | 6/2001 | Van Gompel et al. |
| 6,251,097 | B1 | 6/2001 | Kline et al. |

(56) References Cited

U.S. PATENT DOCUMENTS

| | | | |
|---|---|---|---|
| 6,254,583 B1 * | 7/2001 | Coates | 604/385.14 |
| 6,258,308 B1 | 7/2001 | Brady et al. | |
| 6,278,037 B1 | 8/2001 | Schmidt et al. | |
| 6,287,169 B1 | 9/2001 | Willms et al. | |
| 6,291,039 B1 | 9/2001 | Combe et al. | |
| 6,307,119 B1 | 10/2001 | Cammarota et al. | |
| 6,368,444 B1 | 4/2002 | Jameson et al. | |
| 6,414,215 B1 | 7/2002 | Roe | |
| 6,420,627 B1 | 7/2002 | Ohnishi et al. | |
| 6,423,042 B1 | 7/2002 | Sasaki | |
| 6,423,043 B1 | 7/2002 | Gustafsson | |
| 6,432,098 B1 | 8/2002 | Kline et al. | |
| 6,468,257 B1 | 10/2002 | Ono et al. | |
| 6,482,191 B1 | 11/2002 | Roe et al. | |
| 6,514,362 B1 | 2/2003 | Zuckerman et al. | |
| 6,526,631 B1 | 3/2003 | Alberg et al. | |
| 6,547,773 B2 | 4/2003 | Kleinschmidt et al. | |
| 6,547,774 B2 | 4/2003 | Ono et al. | |
| 6,562,016 B2 | 5/2003 | Shinkai | |
| 6,575,951 B1 | 6/2003 | Ono et al. | |
| 6,579,273 B2 | 6/2003 | Dupuy | |
| 6,623,466 B1 | 9/2003 | Richardson | |
| 6,669,618 B2 | 12/2003 | Reising et al. | |
| 6,680,422 B2 | 1/2004 | Roe | |
| 6,709,423 B1 | 3/2004 | Herrlein et al. | |
| 6,716,441 B1 | 4/2004 | Osborne et al. | |
| 6,764,477 B1 | 7/2004 | Chen et al. | |
| 6,764,478 B2 | 7/2004 | Ashton et al. | |
| 6,786,895 B1 | 9/2004 | Schmitz | |
| 6,794,023 B1 | 9/2004 | Melik et al. | |
| 6,807,685 B1 | 10/2004 | Hasegawa et al. | |
| 6,811,643 B2 | 11/2004 | McAmish et al. | |
| 6,817,992 B1 | 11/2004 | Sassak et al. | |
| 6,821,612 B1 | 11/2004 | Melik et al. | |
| 6,843,949 B2 | 1/2005 | Brady et al. | |
| 6,878,647 B1 | 4/2005 | Rezai et al. | |
| 6,884,494 B1 | 4/2005 | Curro et al. | |
| 6,890,872 B2 | 5/2005 | Bond et al. | |
| 6,893,388 B2 | 5/2005 | Reising et al. | |
| 6,905,987 B2 | 6/2005 | Noda et al. | |
| 6,921,393 B2 | 7/2005 | Tears et al. | |
| 6,936,039 B2 | 8/2005 | Kline et al. | |
| 6,964,720 B2 | 11/2005 | Schneider et al. | |
| 6,966,720 B2 | 11/2005 | Moss | |
| 6,980,872 B2 | 12/2005 | Kano et al. | |
| 7,037,569 B2 | 5/2006 | Curro et al. | |
| 7,060,149 B2 | 6/2006 | Ortega et al. | |
| 7,101,359 B2 | 9/2006 | Kline et al. | |
| 7,166,095 B1 | 1/2007 | Coates | |
| 7,175,613 B2 | 2/2007 | Sugiyama et al. | |
| 7,211,531 B2 | 5/2007 | Schneider et al. | |
| 7,223,818 B2 | 5/2007 | Autran et al. | |
| 7,250,549 B2 | 7/2007 | Richlen et al. | |
| 7,264,615 B2 | 9/2007 | Sherrod et al. | |
| 7,344,526 B2 | 3/2008 | Yang et al. | |
| 7,387,620 B2 | 6/2008 | Watanabe et al. | |
| 7,407,468 B2 | 8/2008 | Reising et al. | |
| 7,458,961 B2 | 12/2008 | Carstens | |
| 7,462,173 B2 | 12/2008 | Carstens | |
| 7,481,801 B2 | 1/2009 | Carstens | |
| 7,491,196 B2 | 2/2009 | Frank et al. | |
| 7,537,587 B2 | 5/2009 | Carstens | |
| 7,576,019 B2 | 8/2009 | Bond et al. | |
| 7,591,811 B2 | 9/2009 | Wilkinson | |
| 7,629,501 B2 * | 12/2009 | Labit et al. | 604/372 |
| 7,666,175 B2 | 2/2010 | Trennepohl | |
| 7,695,463 B2 | 4/2010 | Lavon et al. | |
| 7,771,406 B2 | 8/2010 | Mueller et al. | |
| 7,771,408 B2 | 8/2010 | Mueller et al. | |
| 7,776,770 B2 | 8/2010 | Wang et al. | |
| 7,776,771 B2 | 8/2010 | Autran et al. | |
| 7,820,875 B2 | 10/2010 | Roe et al. | |
| 7,824,387 B2 | 11/2010 | LaVon | |
| 7,833,211 B2 | 11/2010 | Mansfield | |
| 7,842,627 B2 | 11/2010 | Gao et al. | |
| 7,872,169 B2 | 1/2011 | Ruiz et al. | |
| 7,875,014 B2 | 1/2011 | Hendren et al. | |
| 7,887,527 B2 | 2/2011 | Hayashi et al. | |
| 7,914,507 B1 | 3/2011 | Magee | |
| 7,993,322 B2 | 8/2011 | Brud et al. | |
| 8,066,685 B2 | 11/2011 | Olson et al. | |
| 8,118,801 B2 | 2/2012 | Macura et al. | |
| 8,158,043 B2 | 4/2012 | Gibson et al. | |
| 8,206,366 B2 | 6/2012 | Datta et al. | |
| 8,262,635 B2 | 9/2012 | Labit et al. | |
| 8,377,023 B2 | 2/2013 | Sawyer et al. | |
| 8,585,667 B2 | 11/2013 | Roe et al. | |
| 2002/0010452 A1 | 1/2002 | Dupuy | |
| 2002/0035747 A1 | 3/2002 | Kusibojoska et al. | |
| 2002/0128619 A1 | 9/2002 | Carlbark et al. | |
| 2003/0055394 A1 | 3/2003 | Gibbs | |
| 2003/0088220 A1 | 5/2003 | Molander et al. | |
| 2003/0091807 A1 | 5/2003 | Desai et al. | |
| 2003/0114805 A1 | 6/2003 | Rainville et al. | |
| 2003/0125701 A1 | 7/2003 | Widlund | |
| 2003/0163104 A1 | 8/2003 | Tears et al. | |
| 2003/0233082 A1 | 12/2003 | Kline et al. | |
| 2004/0023771 A1 | 2/2004 | Reising et al. | |
| 2004/0127867 A1 | 7/2004 | Odorzynski et al. | |
| 2005/0033258 A1 | 2/2005 | Suzuki et al. | |
| 2005/0096624 A1 | 5/2005 | Hoshino et al. | |
| 2005/0148974 A1 | 7/2005 | Datta et al. | |
| 2005/0164587 A1 | 7/2005 | Melik et al. | |
| 2005/0177123 A1 | 8/2005 | Catalan | |
| 2005/0215965 A1 | 9/2005 | Schmidt et al. | |
| 2005/0215968 A1 | 9/2005 | Henderson | |
| 2005/0215970 A1 | 9/2005 | Kline et al. | |
| 2005/0215971 A1 | 9/2005 | Roe et al. | |
| 2005/0234411 A1 | 10/2005 | Ashton et al. | |
| 2006/0035055 A1 | 2/2006 | Schneider et al. | |
| 2006/0047260 A1 | 3/2006 | Ashton et al. | |
| 2006/0058766 A1 | 3/2006 | Mueller et al. | |
| 2006/0069372 A1 | 3/2006 | Chakravarty et al. | |
| 2006/0087053 A1 | 4/2006 | O'Donnell et al. | |
| 2006/0095012 A1 | 5/2006 | Cohen | |
| 2006/0106356 A1 | 5/2006 | McVicker et al. | |
| 2006/0107505 A1 | 5/2006 | Desai et al. | |
| 2006/0129114 A1 | 6/2006 | Mason et al. | |
| 2006/0129116 A1 | 6/2006 | Hughes et al. | |
| 2006/0178652 A1 | 8/2006 | Miller | |
| 2006/0189956 A1 | 8/2006 | Catalan | |
| 2006/0229582 A1 | 10/2006 | LaVon | |
| 2006/0247599 A1 | 11/2006 | Mullen et al. | |
| 2006/0264865 A1 | 11/2006 | Carstens | |
| 2006/0264867 A1 | 11/2006 | Carstens | |
| 2006/0264868 A1 | 11/2006 | Carstens | |
| 2006/0264869 A1 | 11/2006 | Carstens | |
| 2006/0264870 A1 | 11/2006 | Carstens | |
| 2006/0264871 A1 | 11/2006 | Carstens | |
| 2006/0264872 A1 | 11/2006 | Carstens | |
| 2006/0264873 A1 | 11/2006 | Carstens | |
| 2006/0264874 A1 | 11/2006 | Carstens | |
| 2006/0264877 A1 | 11/2006 | Carstens | |
| 2006/0264878 A1 | 11/2006 | Carstens | |
| 2006/0264879 A1 | 11/2006 | Carstens | |
| 2006/0264880 A1 | 11/2006 | Carstens | |
| 2006/0264881 A1 | 11/2006 | Carstens | |
| 2006/0264882 A1 | 11/2006 | Carstens | |
| 2006/0264883 A1 | 11/2006 | Carstens | |
| 2006/0264884 A1 | 11/2006 | Carstens | |
| 2006/0264885 A1 | 11/2006 | Carstens | |
| 2006/0282056 A1 | 12/2006 | McDonald | |
| 2006/0293637 A1 | 12/2006 | La Von et al. | |
| 2007/0005038 A1 | 1/2007 | Mansfield et al. | |
| 2007/0032772 A1 | 2/2007 | Ehrnsperger et al. | |
| 2007/0123834 A1 | 5/2007 | McDowall et al. | |
| 2007/0142798 A1 | 6/2007 | Goodlander et al. | |
| 2007/0142816 A1 | 6/2007 | Carstens | |
| 2007/0191806 A1 | 8/2007 | Mueller et al. | |
| 2007/0203301 A1 | 8/2007 | Autran et al. | |
| 2007/0239130 A1 | 10/2007 | Trennepohl | |
| 2007/0249254 A1 | 10/2007 | Mansfield | |
| 2007/0287348 A1 | 12/2007 | Autran et al. | |
| 2007/0287982 A1 | 12/2007 | Lodge et al. | |

(56) References Cited

U.S. PATENT DOCUMENTS

| | | |
|---|---|---|
| 2007/0287983 A1 | 12/2007 | Lodge et al. |
| 2007/0293111 A1 | 12/2007 | Mansfield |
| 2008/0004582 A1 | 1/2008 | Lodge et al. |
| 2008/0004583 A1 | 1/2008 | Desai et al. |
| 2008/0004584 A1 | 1/2008 | Langdonl et al. |
| 2008/0004586 A1 | 1/2008 | Lodge et al. |
| 2008/0004587 A1 | 1/2008 | Lodge et al. |
| 2008/0004589 A1 | 1/2008 | Roe et al. |
| 2008/0004590 A1 | 1/2008 | Lodge et al. |
| 2008/0004591 A1 | 1/2008 | Desai et al. |
| 2008/0004592 A1 | 1/2008 | Lodge et al. |
| 2008/0004593 A1 | 1/2008 | Lodge et al. |
| 2008/0009817 A1 | 1/2008 | Norrby |
| 2008/0015537 A1 | 1/2008 | Lodge et al. |
| 2008/0033388 A1 | 2/2008 | Muellerg et al. |
| 2008/0045917 A1 | 2/2008 | Autran et al. |
| 2008/0081854 A1 | 4/2008 | Wang et al. |
| 2008/0114327 A1 | 5/2008 | Barge |
| 2008/0119813 A1 | 5/2008 | Carstens |
| 2008/0119814 A1 | 5/2008 | Carstens |
| 2008/0119815 A1 | 5/2008 | Carstens |
| 2008/0119816 A1 | 5/2008 | Carstens |
| 2008/0125739 A1 | 5/2008 | Lodge et al. |
| 2008/0138599 A1 | 6/2008 | Gao et al. |
| 2008/0176473 A1 | 7/2008 | Wang et al. |
| 2008/0188822 A1 | 8/2008 | Lodge et al. |
| 2008/0215028 A1 | 9/2008 | Brown et al. |
| 2008/0224351 A1 | 9/2008 | Curro et al. |
| 2008/0287983 A1 | 11/2008 | Smith et al. |
| 2008/0312617 A1 | 12/2008 | Hundorf et al. |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312628 A1 | 12/2008 | Hundorf et al. |
| 2008/0319407 A1 | 12/2008 | Erdem et al. |
| 2009/0069722 A1 | 3/2009 | Flaction et al. |
| 2009/0069772 A1 | 3/2009 | Sauer et al. |
| 2009/0069773 A1 | 3/2009 | Sauer et al. |
| 2009/0069774 A1 | 3/2009 | Sauer et al. |
| 2009/0069775 A1 | 3/2009 | Sauer et al. |
| 2009/0069777 A1 | 3/2009 | Sauer et al. |
| 2009/0069778 A1 | 3/2009 | Sauer et al. |
| 2009/0069779 A1 | 3/2009 | Sauer et al. |
| 2009/0069781 A1 | 3/2009 | Sauer et al. |
| 2009/0069782 A1 | 3/2009 | Sauer et al. |
| 2009/0127742 A1 | 5/2009 | Qureshi et al. |
| 2009/0216209 A1 | 8/2009 | Ekstrom |
| 2010/0004616 A1 | 1/2010 | Nakamura |
| 2010/0005570 A1 | 1/2010 | Rachman |
| 2010/0179495 A1 | 7/2010 | Roe |
| 2010/0179496 A1 | 7/2010 | Roe et al. |
| 2010/0179498 A1 | 7/2010 | Roe |
| 2010/0179499 A1 | 7/2010 | Roe |
| 2010/0179500 A1 | 7/2010 | Roe et al. |
| 2010/0179501 A1 | 7/2010 | Roe et al. |
| 2010/0179502 A1 | 7/2010 | Roe |
| 2010/0179503 A1 | 7/2010 | Roe |
| 2010/0201024 A1 | 8/2010 | Gibson et al. |
| 2010/0331803 A1 | 12/2010 | Saito |
| 2011/0137277 A1 | 6/2011 | Hough et al. |
| 2012/0022491 A1 | 1/2012 | Roe |
| 2012/0049404 A1 | 3/2012 | Gibson et al. |
| 2013/0006207 A1 | 1/2013 | Roe et al. |
| 2013/0102986 A1 | 4/2013 | Ruiz et al. |
| 2014/0013490 A1 | 1/2014 | Evenson et al. |
| 2014/0018756 A1 | 1/2014 | De Bruin et al. |
| 2014/0018757 A1 | 1/2014 | De Bruin et al. |
| 2014/0018760 A1 | 1/2014 | Orchard, IV et al. |
| 2014/0018761 A1 | 1/2014 | Orchard, IV et al. |
| 2014/0018762 A1 | 1/2014 | Vignali et al. |
| 2014/0018763 A1 | 1/2014 | Evenson et al. |
| 2014/0018764 A1 | 1/2014 | Johnston et al. |

FOREIGN PATENT DOCUMENTS

| | | |
|---|---|---|
| CA | 2221209 | 11/1996 |
| CA | 2 365 577 | 6/2003 |
| DE | 103 03 903 | 11/2003 |
| EP | 0 023 804 | 2/1981 |
| EP | 0 187 726 | 7/1986 |
| EP | 319314 | 6/1989 |
| EP | 0667136 | 8/1995 |
| EP | 549988 | 6/1998 |
| EP | 796069 | 8/2000 |
| EP | 763353 | 6/2002 |
| FR | 2532337 | 3/1984 |
| GB | 112638 | 1/1918 |
| GB | 2 440 314 | 1/2008 |
| JP | 57-181003 | 11/1982 |
| JP | 57-184864 | 12/1982 |
| JP | 59-5656 | 1/1984 |
| JP | 59-5657 | 1/1984 |
| JP | 59-147214 | 9/1984 |
| JP | 59-147215 | 9/1984 |
| JP | 60-87139 | 6/1985 |
| JP | 60-91191 | 6/1985 |
| JP | 61-98628 | 6/1986 |
| JP | 62-110903 | 7/1987 |
| JP | 03-091325 | 1/1990 |
| JP | 4-7792 | 11/1990 |
| JP | 06-178795 | 1/1993 |
| JP | 2001-346826 | 12/2001 |
| JP | 2002-325786 | 11/2002 |
| JP | 2003-038564 | 2/2003 |
| JP | 2003-093438 | 4/2003 |
| JP | 2003-190213 | 7/2003 |
| JP | 2004-261332 | 9/2004 |
| JP | 2005-6827 | 1/2005 |
| JP | 2005-111119 | 4/2005 |
| JP | 2005-118533 | 5/2005 |
| JP | 3109189 | 5/2005 |
| JP | 2007-244506 | 3/2006 |
| JP | 2008-237231 | 10/2008 |
| JP | 2009-153736 | 7/2009 |
| JP | 47-40720 | 8/2011 |
| WO | WO-90/08524 | 8/1990 |
| WO | WO-91/16871 | 11/1991 |
| WO | WO-92/01431 | 2/1992 |
| WO | WO-92/15444 | 9/1992 |
| WO | WO-94/15563 | 7/1994 |
| WO | WO-94/15663 | 7/1994 |
| WO | WO-95/10992 | 4/1995 |
| WO | WO-95/16746 | 6/1995 |
| WO | WO-96/17572 | 6/1996 |
| WO | WO-96/24319 | 8/1996 |
| WO | WO-96/32912 | 10/1996 |
| WO | WO-00/65348 | 11/2000 |
| WO | WO-02/066086 | 8/2002 |
| WO | WO-2004/060229 | 7/2004 |
| WO | WO-2005/039469 | 5/2005 |
| WO | WO-2005/052052 | 6/2005 |
| WO | WO-2005/096855 | 10/2005 |
| WO | WO-2005/097031 | 10/2005 |
| WO | WO-2008/030984 | 3/2008 |
| WO | WO-2008/120959 | 10/2008 |
| WO | WO-2008/142634 | 11/2008 |
| WO | WO-2010/053006 | 5/2010 |
| WO | WO 2010078661 | 7/2010 |
| WO | WO-2012/167844 | 12/2012 |

OTHER PUBLICATIONS www.gdiapers.com—Web pages dated Nov. 23, 2009.
www.fuzzibunz.com—Web pages dated Nov. 23, 2009.
www.greenmountaindiapers.com—Web pages dated Nov. 23, 2009.
www.bumgenius.com—Web pages dated Nov. 23, 2009.
www.thirstiesbaby.com—Web pages dated Nov. 23, 2009.
www.crickettsdiaper.com—Web pages dated Nov. 23, 2009.

(56) References Cited

OTHER PUBLICATIONS

Archived web page from www.bummis.com, Aug. 8, 2005, obtained via www.waybackmachine.org.
"Green Life; Earth-Friendly Disposable Diaper Lets Parents Flush Away the Guilt", The Oregonian (Apr. 7, 2005).
"Crazy for Cloth: The Benefits of Cotton Diapers", Mothering Magazine (Jan. 1, 2003).
"Not Your Grandma's Diapers", E: The Environmental Magazine (Mar.-Apr. 2006).
"Y2K Babyware: Your Green Guide to Carefree Diapering for Your Millennium Bundle of Joy". The Gazette (Montreal, Quebec) (Oct. 5, 2000).
"The Evolution of Diapers: Cloth Meets Cute for Some Mothers (and Grandmothers), The Changes in Cloth Diapers Have Made Them all the Rage. Learning the Lingo Navigating Cloth" Omaha World Herald (Mar. 22, 2004).
37 photographs (obtained from Marketing Technology Service, Inc.) of a product believed to be a product of Kao Corp. and sold in Japan in 1986 (translations provided by Applicants.
Data Sheet, p. V-17, from "Baby Diaper Design Update—1987", publication of Marketing Technology Service, Inc., product believed to be a product of Kao Corp. sold in Japan in 1986 or 1987.
All Office Actions, Responses and Claims, U.S. Appl. No. 12/687,437.
All Office Actions, Responses and Claims, U.S. Appl. No. 12/687,493.
All Office Actions, Responses and Claims, U.S. Appl. No. 12/687,507.
All Office Actions, Responses and Claims, U.S. Appl. No. 12/687,527.
All Office Actions, Responses and Claims, U.S. Appl. No. 12/687,538.
All Office Actions, Responses and Claims, U.S. Appl. No. 12/687,554.
All Office Actions, Responses and Claims, U.S. Appl. No. 12/785,152.
All Office Actions, Responses and Claims, U.S. Appl. No. 12/785,166.
All Office Actions, Responses and Claims, U.S. Appl. No. 12/785,181.
All Office Actions, Responses and Claims, U.S. Appl. No. 14/053,014.
All Office Actions, Responses and Claims, U.S. Appl. No. 12/841,553.
All Office Actions, Responses and Claims, U.S. Appl. No. 12/841,467.
All Office Actions, Responses and Claims, U.S. Appl. No. 13/859,015.
All Office Actions, Responses and Claims, U.S. Appl. No. 12/841,600.
All Office Actions, Responses and Claims, U.S. Appl. No. 14/014,440.

* cited by examiner

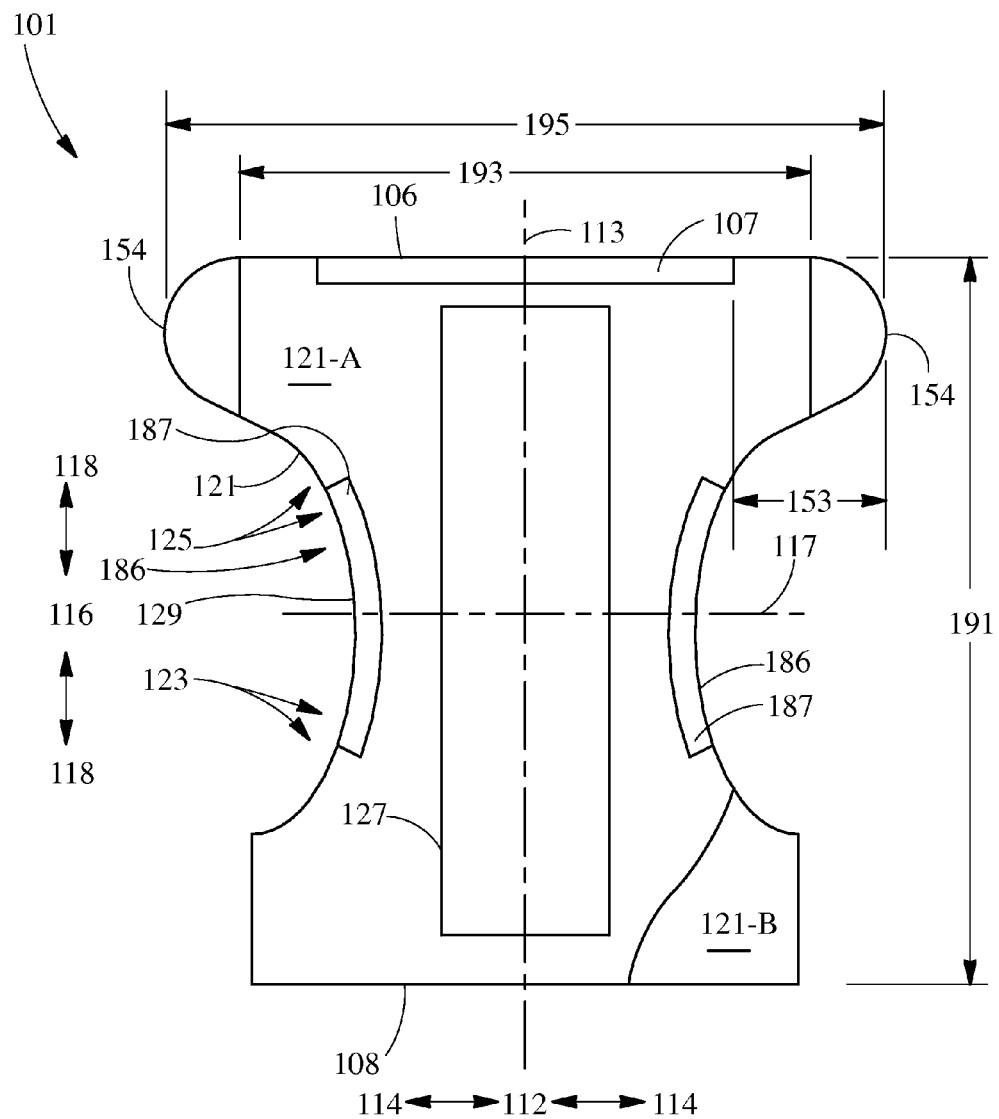

REUSABLE OUTER COVERS FOR WEARABLE ABSORBENT ARTICLES

CROSS REFERENCE TO RELATED APPLICATIONS

This application claims the benefit of U.S. provisional patent application 61/144,883 filed Jan. 15, 2009, the substance of which is hereby incorporated by reference.

FIELD

In general, embodiments of the present disclosure relate to reusable absorbent articles. In particular, embodiments of the present disclosure relate to wearable absorbent articles with reusable outer covers.

BACKGROUND

Wearable absorbent articles include reusable diapers and reusable incontinence undergarments. A wearable absorbent article can receive and contain bodily waste while being worn by a wearer. Some wearable absorbent articles have reusable outer covers. Reusable outer covers can be made with various materials in a number of configurations. The design of a reusable outer cover can affect the way that a wearable absorbent article fits on a wearer. Unfortunately, some reusable outer covers perform poorly after being laundered. As an example, some reusable outer covers shrink and/or stretch when laundered. This change in size and/or shape can cause wearable absorbent articles to sag or slip down on a wearer, resulting in a wearable absorbent article that can feel uncomfortable, look unattractive, and perform poorly as the article tends to leak. As another example, some reusable outer covers experience substantial changes in elasticity when laundered. These changes may require more force to stretch a leg opening, resulting in skin marking, or may result in a loss in force that could cause gapping at a leg opening. As a further example, some reusable outer covers experience a reduction in unload forces, which can could cause poor sustained fit and leakage.

BRIEF DESCRIPTION OF THE DRAWINGS

FIG. 1 illustrates a plan view of an inside of a front fastenable wearable absorbent article with a reusable outer cover.

DETAILED DESCRIPTION

Embodiments of the present disclosure include reusable outer covers that perform well after being laundered. The designs of these outer covers help prevent wearable absorbent articles from sagging or slipping down on a wearer. As a result, wearable absorbent articles with the reusable outer covers of the present disclosure can feel comfortable, look attractive, and perform well as the articles tend to stay in place on wearers and not leak.

Absorbent articles include products for sanitary protection, for hygienic use, and the like. Some absorbent articles are wearable. A wearable absorbent article is configured to be worn on or around a lower torso of a body of a wearer. Examples of wearable absorbent articles include diapers, training pants, and incontinence undergarments.

A wearable absorbent article can include an absorbent core. Throughout the present disclosure, the term absorbent core refers to a part of a wearable absorbent article configured to absorb bodily exudates received into the article from a body of a wearer. An absorbent core can be configured in various ways, as will be understood by one of ordinary skill in the art. An absorbent core can include one or more absorbent materials, such as wood pulp and/or superabsorbent particles, and may include one or more additional compositions, materials, or structures for receiving, containing, storing, and/or treating bodily waste, as known in the art. Further, an absorbent core may include one or more of compositions such as lotions, perfumes, and sensates, on an outer surface and/or within the assembly. An absorbent core can be configured as a bucket-shaped absorbent core, a removable absorbent core, a replaceable absorbent core, an absorbent core insert, etc. An absorbent core can be part of an absorbent core assembly, comprising one or more layers such as a liquid-permeable topsheet, an acquisition layer, a distribution layer, a storage layer, and a liquid impermeable backsheet. An absorbent core assembly may also include one or more of various structures, such as barrier leg cuffs, a feces containment compartment, a wetness indicator, fasteners for retaining the core within an article, disposal tapes, etc. In various embodiments, an absorbent core can be affixed directly to the inside surface of an outer cover.

In various embodiments, an absorbent core can be configured as described in U.S. applications Ser. Nos. 12/141,122; 12/141,124; 12/141,126; 12/141,128; 12/141,130; 12/141, 132; 12/141,134; 12/141,141; 12/141,143; and 12/141,146, each of which is hereby incorporated by reference. These applications generally describe absorbent core constructions that minimize or eliminate the need for and inclusion of airfelt or other forms of cellulose fiber in combination with super absorbent particles.

A wearable absorbent article can also include an outer cover. Throughout the present disclosure, the term outer cover refers to a part of a wearable absorbent article forming an outer surface of the article (sometimes referred to as a backsheet), extending beyond the edges of the absorbent core, usually covering a significant portion of the buttocks of the wearer, and generally shaped to resemble the appearance of an undergarment. An outer cover can be configured in various ways, as described herein. In various embodiments, an outer cover can coincide with and/or define a chassis of a wearable absorbent article.

Some absorbent articles are disposable. A disposable absorbent article is configured to be disposed of after a single use (e.g., not intended to be reused, restored, or laundered). Examples of disposable absorbent articles include disposable diapers, disposable training pants, disposable incontinence undergarments, as well as feminine care pads and liners.

Some absorbent articles are reusable. The term reusable, as used herein, means that a referenced material, component, or all of an absorbent article is configured to be restored and/or reused for more than one usage cycle (e.g. a diaper change). In some reusable absorbent articles, part, or parts, or substantially all, or all of the articles may be launderable or laundering resistant, as defined and described herein. As an example, a wearable absorbent article can include an outer cover that is launderable or laundering resistant. In other reusable absorbent articles, part, or parts, or substantially all, or all of the articles may not be launderable or may not be laundering resistant. For example, an absorbent article can be configured as a reusable absorbent article by using materials, such as nonwovens, that are used in disposable articles, such as diapers.

In various embodiments, a reusable outer cover can be configured to perform various functions, which provide various benefits to a wearer of the article and/or to a care giver for the wearer. In various embodiments, a reusable outer cover can be configured to provide liquid impermeability, which can help the absorbent article contain bodily waste. In various embodiments, a reusable outer cover can be configured to provide vapor permeability (e.g. breathability), which can help the wearer maintain healthy skin. In various embodiments, a reusable outer cover can be configured to be elastically extensible, inelastically extensible, and/or inextensible, in one or more particular directions. In various embodiments, at least a portion of a reusable outer cover, such as a portion of an inner layer, may be absorbent to control minor leakage events from the absorbent core.

Specifically, part, or parts, or substantially all, or all of a reusable outer cover thereof can be configured to extend and relax to particular degrees, while the article is being applied to a wearer, while the article is being worn by a wearer, and while the article is containing bodily waste. A reusable outer cover can be configured to extend easily while the article is being applied to a wearer, to help facilitate application. A reusable outer cover can also be configured to extend adequately while the article is being worn, to help accommodate the wearer's movement while provide a conforming fit. A reusable outer cover can further be configured to relax (i.e. contract), properly with sufficient tension to provide sustained fit while the article is being worn, and to help support the absorbent core. It is contemplated that any reusable outer cover disclosed herein can be used with any embodiment of a wearable absorbent article disclosed herein.

The term launderable, as used herein, means that a referenced material, component, or all of an absorbent article is configured to withstand a large number (e.g. at least 10, in some embodiments up to 50, in other embodiments more than 50) of cycles of machine washing and machine drying (as defined by AATCC Test Method 124-2001 as described herein), without significant degradation to the appearance or performance of the article that would render it unsuitable for its intended functionality and/or use. As used herein, the term "wash" or "wash cycle" refers to a cycle of machine washing and machine drying, as described above. Since hand-washing and line-drying are typically much less stressful on an absorbent article than machine washing and machine drying, it is expected that a material, component, or article that is machine washable and machine dryable, should also be hand-washable and hand-dryable for at least as many cycles. As an example, a reusable wearable absorbent article can include an outer cover that is launderable. Launderable articles are designed to be suitable for use after many washings, similar to types of clothing.

The term laundering resistant, as used herein, means that a referenced material, or component, or all of an absorbent article is configured to withstand a small number (e.g. at least one, in some embodiments up to 5, in other embodiments more than 5) of cycles of machine washing and drying (as defined by AATCC Test Method 124-2001 and as described herein), without significant degradation to the appearance or performance of the article that would render it unsuitable for its intended functionality and/or use. As an example, a reusable wearable absorbent article can include an outer cover that is laundering resistant. Laundering resistant articles generally experience degradation after fewer laundering cycles than launderable articles. For example, a laundering resistant material may experience significant degradation in appearance or performance after 5 or 10 wash cycles.

FIG. 1 illustrates a plan view of an inside (wearer-facing side) of a front fastenable wearable absorbent article 101. While the present disclosure refers to front fastenable wearable absorbent articles, the present disclosure also contemplates alternate embodiments of wearable absorbent articles, as described herein, wherein the wearable absorbent articles are rear-fastenable or side-fastenable. Thus, each embodiment of a wearable absorbent article of the present disclosure that is described as front fastenable can also be configured to be rear fastenable, as will be understood by one of ordinary skill in the art.

In FIG. 1, a longitudinal centerline 113 and a lateral centerline 117 provide lines of reference for referring to relative locations of parts of the wearable absorbent article 101. When a first part is nearer to the longitudinal centerline 113 than a second part, the first part can be considered laterally inboard 112 to the second part. Similarly, the second part can be considered laterally outboard 114 from the first part. When a third part is nearer to the lateral centerline 117 than a fourth part, the third part can be considered longitudinally inboard 116 to the fourth part. Similarly, the fourth part can be considered longitudinally outboard 118 from the third part. FIG. 1 includes arrows indicating relative directions for laterally inboard 112, laterally outboard 114, longitudinally inboard 116, and longitudinally outboard 118, with respect to the wearable absorbent article 101. Throughout the present disclosure, unless otherwise stated, a reference to a longitudinal dimension, measurement, line, or direction refers to a dimension, measurement, line, or direction substantially or completely parallel to the longitudinal centerline 113, and a reference to a lateral dimension, measurement, line, or direction refers to a dimension, measurement, line, or direction substantially or completely parallel to the lateral centerline 117.

The wearable absorbent article 101 includes a outer cover 121, defining the outermost edges of the article 101. The outer cover 121 includes an inner layer 121-A and an outer layer 121-B; in FIG. 1, the inner layer 121-A is shown as partially broken away to show the outer layer 121-B. The outer cover 121 also includes a front 123, and a back 125. It is contemplated that, in various embodiments, the outer cover 121 can be configured as any reusable outer cover disclosed herein, including a launderable outer cover and/or a laundering resistant outer cover.

The front 123 is a portion of the wearable absorbent article 101 disposed generally proximate to and/or below the belly of a wearer, when the wearable absorbent article 101 is worn by the wearer. A reference to the "front" can mean the front itself, part, or parts, or substantially all, or all of an element in the front, and/or a disposition in the front, depending on the context of the reference. The back 125 is a portion of the wearable absorbent article 101 disposed generally proximate to and/or below the back of a wearer, when the wearable absorbent article 101 is worn by the wearer. A reference to the "back" can mean the back itself, part, or parts, or substantially all, or all of an element in the back, and/or a disposition in the back, depending on the context of the reference. The lateral centerline 117 of the wearable absorbent article 101 forms a boundary between the front 123 and the back 125. The front and back terminology described above is used for wearable absorbent articles throughout the present disclosure, unless otherwise indicated. The wearable absorbent article 101 also includes an absorbent core 127 extending from the front 123 to the back 125.

The outer cover 121 also includes a back waist edge 106 and a back elastic waist band 107. The back elastic waist band 107 is disposed proximate to the back waist edge 106 and extends laterally across a portion of the back 125. The outer cover 121 also includes a front waist edge 108. In various embodiments, an outer cover can include a front elastic waist band disposed proximate to a front waist edge and extending laterally across a portion of the front. The outer cover 121 also includes longitudinal sides with leg cuff portions 186, which at least partially encircle a leg of a wearer when the article 101 is worn. Leg elastic bands 187 are disposed proximate to the leg cuff portions 186 and extend longitudinally to a portion of the front 123 and a portion of the back 125.

The outer cover 121 further includes a side 152, a side ear 153, and fasteners 154. The side 152 is disposed in the back 125, laterally outboard from a narrowest portion of the outer cover 121. Although the side 152 is illustrated as to the right of the longitudinal centerline 113, the outer cover 121 also includes another side, of the same configuration, to the left of the longitudinal centerline 113. The side 152 includes the side ear 153, which is the portion of the outer cover 121 laterally extending outward from the longitudinal side of the outer cover 121, as illustrated by the phantom line, which is provided for reference. In various embodiments, part, or parts, or substantially all, or all of a side ear may be formed by a portion of an outer cover or may be formed by a separate element attached to an outer cover. The outer cover 121 includes a second side ear as part of the other side. Each of the side ears 153 includes a fastener 154, for fastening the back 125 to the front 123.

The outer cover 121 includes an overall longitudinal length 191 measured along the longitudinal centerline from the back waist edge 106 to the front waist edge 108. The outer cover 121 also includes an overall lateral width of the back waist region 193, measured across the widest portion of the back 125. The outer cover 121 further includes a lateral width between fasteners 195 measured between the farthest laterally inboard points along the edges of the fasteners 154 on the back ears 154 of the outer cover 121. The dimensions 191, 193, and 195 are the dimensions measured in the test methods, described herein. Analogous dimensions can be similarly located in an outer cover for a pant-type wearable absorbent article, as will be understood by one of skill in the art.

Exemplary Launderable Outer Cover

Following is a description of an exemplary launderable outer cover for use in a front fastenable wearable absorbent article. The exemplary launderable outer cover includes an outer layer, an inner layer, left and right side leg bands, front and back waist bands, an anchoring band, a landing zone, side ear fasteners, side ear stiffeners, and absorbent core fastening elements.

Throughout the present disclosure, the term right side refers to a side of a material that will be on the outside of the completed article, and the term wrong side refers to a side of a material that will be on the inside of the completed article (or, in embodiments having multiple layers, between layers of the completed article). When complete, the right side of the outer layer will be the garment-facing side and the right side of the inner layer will be the wearer-facing side.

Each element of the exemplary launderable outer cover is formed from one or more particular materials. The outer layer material is a soft and stretchable knit fabric made of Modal with Lycra. For example, the outer layer material can be 95% Modal and 5% Lycra. The inner layer material is made from two materials. The inner layer material that is configured to be disposed in a back of the article is configured to be laterally stretchable, to provide a comfortable fit. The back inner layer material is a soft and stretchable knit fabric made of polyester with Spandex. For example, the inner layer material can be 94% polyester and 6% Spandex. The inner layer material that is configured to be disposed in a crotch and front of the article is configured to be hydrophobic, to resist urine penetration. For example, the inner layer material can be 90% Nylon Tricot and 10% Spandex.

The leg and waist bands are formed from inner material, which is elastic, and an outer material, which is a soft, extensible fabric. For example, the inner elastic band material can be natural elastic, about 10 mm wide. The inner elastic band material is similar to the back inner layer material. The outer fabric band material is similar to the outer layer material.

The anchoring band material is a strip of stretchable knit fabric made of polyester with Spandex. For example, the stretchable knit fabric can be 90% polyester and 10% Spandex, 25 mm wide. The anchoring band material is configured to have a higher modulus of elasticity and a lower elastic Hysteresis than the outer layer material. The landing zone and the side ear fasteners comprise a mechanical hook and loop fastening system with sewable patches of loops and hooks, respectively. The ear stiffener material is a woven fusible interfacing, to help the ears resist folding or buckling. The absorbent core fastening elements are also patches of loops configured to fasten with hooks on an absorbent core.

To make the exemplary launderable outer cover, first, each material is cut to a desired shape. The outer layer material and the inner layer material are cut to the same shape, which is the overall shape of the outer cover.

For the leg bands, two pieces of the inner elastic band material are cut; each to a length for contractible leg cuff portions of the left or right longitudinal side of the outer cover. For example the length of the inner elastic leg band can be about 220 mm. Also, two pieces of the outer fabric band material are cut; each to a particular length and a width such that each piece of the outer fabric leg band material can be folded in half lengthwise to envelope a piece of the inner elastic leg band material.

Similarly, for the waist bands, two pieces of the inner elastic band material are cut; each to a length for contractible waist edge portions of the front or back end of the outer cover. For example the length of the inner elastic waist band can be about 245 mm. Further, two pieces of the outer fabric band material are cut; each to a particular length and a width so that each piece of the outer fabric waist band material can folded in half lengthwise to envelope a piece of the inner elastic waist band material.

One anchoring band is cut to length to fit from one back side ear to the other back side ear. Two side ear fasteners are cut to fit on the side ears on the back of the outer cover. One landing zone is cut to accommodate the side ear fasteners and to fit on the front of the outer cover. Eight side ear stiffeners are cut to fit inside the side ears on each side in the front and back of the outer cover. Two absorbent core fastener elements are cut to accommodate hooks on an absorbent core.

Second, the cut materials are assembled together. The landing zone is sewn to the right side of front of the outer cover. Four of the side ear stiffeners are fused to wrong side of the outer layer, one each at the left and right side ears on the front and back.

The leg bands are sewn to the wrong side of the inner layer and to the wrong side of the outer layer at the contractible leg cuff portions on the left and right longitudinal sides of the outer cover. During this sewing, a central portion of the each leg band is prestretched while the inner layer and the outer layer are substantially relaxed. For each leg band, the ends of the inner elastic leg band material are secured, but a central portion is free to move inside of the outer fabric leg band material.

Similarly, the waist bands are sewn to the wrong side of the inner layer and to the wrong side of the outer layer at the contractible waist edge portions on the front and back ends of the outer cover. During this sewing, a central portion of the each leg band is prestretched while the inner layer and the outer layer are substantially relaxed. For each waist band, the ends of the inner elastic waist band material are secured, but a central portion is free to move inside of the outer fabric waist band material.

The anchoring band is sewn to the wrong side of the inner layer, at the back side ear and the front side ear. During this sewing, both the anchoring band and the inner layer are substantially relaxed; that is, when they are laid down flat together, neither element is prestretched with respect to the other. A central portion of the anchoring band is not sewn to the inner layer. The side ear fasteners are sewn to the right side of the inner layer, at the left back side ear and the right back side ear. The absorbent core fastening elements are sewn to the right side of front and back of the inner layer. Four of the side ear stiffeners are fused to wrong side of the inner layer, one each at the left and right side ears on the front and back. The inner layer and the outer layer are then sewn together and inverted in order to be right side out. The exemplary launderable outer cover is complete. In the completed outer cover, the central portion of the anchoring band is free to move with respect to the inner layer and the outer layer. Also, in the completed outer cover, the anchoring band is not prestretched with respect to the inner layer or the outer layer.

This exemplary launderable outer cover is intended as a non-limiting example, and can be varied in numerous ways as described below. Any of the elements of the outer cover may comprise one or more subcomponents; that is, an element may be formed of more than one piece or type of material. Either or both layers of the outer cover may comprise a single layer of material or may comprise two or more layers and/or two or more materials. The inner layer may be stretchable in both the lateral and longitudinal directions. The inner layer may be treated to make it more hydrophobic. The inner layer may have varying stretchability, hydrophbicity, and/or breathability across its area.

The outer cover may also have varying stretchability, hydrophbicity, and/or breathability across its area. The outer cover may have no anchoring band or may have any number of anchoring bands or other anchoring system components. As an example, a launderable outer cover can be configured to include one or more elements of an anchoring system, as described in U.S. non-provisional patent application entitled "Reusable Wearable Absorbent Articles with Anchoring Systems," filed on Jan. 14, 2010 under attorney docket number 11225M, which is incorporated herein by reference. As an additional example, a launderable outer cover can be configured to include one or more elements of an anchoring system, as described in U.S. non-provisional patent application entitled "Reusable Wearable Absorbent Articles with Anchoring Subsystems," filed on Jan. 14, 2010 under attorney docket number 11565, which is incorporated herein by reference.

The outer cover may comprise structures to protect the fastening elements during washing (e.g. protective flaps to cover the hooks or areas adjacent the hooks where the fastener may be temporarily affixed). The absorbent core can be connected to the outer cover by any kind of mechanism, such as pockets, cuffs, straps, loops, hook and loop type fasteners, or fasteners of any type, which can be added onto the outer cover and/or the absorbent core. The outer cover may comprise macro fasteners or any other fastening systems as known in the art. The leg and waist band constructions may be single materials, laminates, etc. The leg and waist bands may be affixed to inner layer only or to outer layer only.

In various alternate embodiments, the exemplary launderable outer cover can be varied in numerous other ways with additional and/or alternate materials, structures, configurations, and assembly methods, as will be understood by one of skill in the art.

Launderable outer cover materials may include any natural or synthetic materials known in the diaper, pant, underwear, performance clothing, sport clothing, or general clothing or textile art. These materials may include natural materials such as cotton, wool, bamboo, hemp, silk, rayon, and the like, as well as blends of these materials with synthetic fibers. Exemplary synthetic materials suitable for use in launderable outer covers may include polyester, nylon, Lycra, Spandex, or other elastomers, breathable waterproof materials such as GORE-TEX® (W. L. Gore & Associates, Inc., Elkton, Md.), fabrics comprising microencapsulated phase-change polymer materials such as Outlast ComforTemp fabrics (Outlast Technologies, Boulder, Colo.—see U.S. Pat. Nos. 6,514,362 and 6,207,738 for example), COOLMAX® (INVISTA, Wichita, Kans.), and the like. These materials preferably include at least one fiber-based material, such as a fabric or woven or nonwoven web. However, the outer covers may additionally comprise a film layer to provide enhanced liquid penetration resistance and/or elastic properties to the outer cover. Elastic properties can be added or enhanced via the addition of other materials to the outer cover, including elastic strands, bands, scrims, and the like. Launderable materials may be formed in any known weave or fabric form, including birdseye fabric, terry, fleece, flannel, knits, stretch knits, sherpa, suedecloth, microfleece, satin, velour, Burley knits, and Polartec® Windpro® (Polartec, LLC, Lawrence, Mass.). Knitted textiles, which may be more inherently stretchable and elastic than woven or nonwoven materials, may impart better fit, comfort and/or appearance to the outer cover. Incorporation of fibers of spandex or other elastomer also may also enhance stretchability and elasticity, and thereby impart better fit, comfort and/or appearance to the outer cover, than textiles not including such elastomeric fibers.

Specific suitable examples for launderable outer cover materials include jersey knits of blends of: rayon (93%) and spandex (7%) fibers; modal (94%) and spandex (6%) fibers; cotton and spandex fibers; and bamboo and spandex fibers. Materials that have stretch capability of equal to or greater than about 30%, or 50%, or 100%, or 150%, or even 200% may be desired. Suitable examples of materials may have basis weights of about 0.09-0.15 gram/in.2 per layer, or other basis weights.

Launderable outer cover materials may be selected to impart desired comfort, appearance and performance to a wearable absorbent article. In some circumstances it may be desired to select launderable outer cover materials which are sufficiently inexpensive to allow for disposal, if soiled extensively or damaged, with minimized issues of cost or conscience.

It is contemplated that any launderable outer cover disclosed herein can be used with any embodiment of a wearable absorbent article disclosed herein. The exemplary launderable outer cover can also be adapted for use in a pant type wearable absorbent article.

Exemplary Laundering Resistant Outer Cover

Following is a description of an exemplary laundering resistant outer cover for use in a front fastenable wearable absorbent article. The exemplary launderable outer cover includes a tri-laminate comprising two extensible nonwoven materials and an elastically stretchable film sandwiched in between the nonwovens. The first extensible nonwoven forms the garment-facing side of the outer cover, while the second extensible nonwoven forms the wearer-facing side of the outer cover. The first extensible nonwoven is a 27 gsm HEC nonwoven, such as Excell Style 382D, available from Fiberweb/BBA. The elastically stretchable film comprises a 27 gsm Vistamaxx film (the resin of which is available from Exxon-Mobil) with a polyethylene skin layer of about 5 gsm. The second extensible nonwoven is a 22 gsm nonwoven, such as Sofspan 200 available from Fiberweb France.

The film and the second nonwoven are extrusion bonded together to form a bilaminate. The bilaminate is available as material M18-2038C from Clopay Corp. The first nonwoven is adhesively bonded to the film side of the bilaminate via 0.0006 g/in2 of 2031 spiral adhesive available from Bostik, to form the tri-laminate. The outer cover also includes an anchoring band, disposed within the tri-laminate. The anchoring band is a strip of elastomer film, about 25 mm wide, disposed in the back waist region of the outer cover, oriented parallel to the lateral centerline of the outer cover and extending from the fastener on one side of the outer cover to the fastener on the other side of the outer cover. The trilaminate outer cover is then mechanically activated (i.e., incrementally stretched in a lateral direction) using a ringrolling process. In the ringrolling process, the ringroll tooth pitch is 0.100" and the depth of engagement is 0.158".

As an example, a laundering resistant cover can be configured to include one or more elements of an anchoring system, as described in U.S. non-provisional patent application entitled "Reusable Wearable Absorbent Articles with Anchoring Systems," filed on Jan. 14, 2010 under attorney docket number 11225M, which is incorporated herein by reference. As an additional example, a laundering resistant cover can be configured to include one or more elements of an anchoring system, as described in U.S. non-provisional patent application entitled "Reusable Wearable Absorbent Articles with Anchoring Subsystems," filed on Jan. 14, 2010 under attorney docket number 11565, which is incorporated herein by reference.

This exemplary laundering resistant outer cover is intended as a non-limiting example. In alternate embodiments, the exemplary laundering resistant outer cover can be varied in numerous ways with additional and/or alternate materials, structures, configurations, and assembly methods, as will be understood by one of skill in the art.

Outer covers that are laundering resistant may still be sufficiently inexpensive to allow them to be disposed without issues of cost or conscience if soiled extensively or damaged. Laundering resistant outer cover materials may include any of the materials described herein, including one or more materials contemplated for use in launderable or disposable outer covers. If materials for use in launderable outer covers are selected, typically less expensive, lower quality (e.g., lower basis weight, less optimal fiber quality) versions may be employed, to form outer covers that are laundering resistant. If materials for use in disposable articles (e.g. disposable diapers) are selected, higher basis weights and/or quality of materials may be appropriate. Blends or laminates of such materials are also contemplated for laundering resistant outer covers.

As an example, a disposable wearable absorbent article design can be modified to make the article laundering resistant. For instance, a wearable absorbent article constructed as described in US patent application publication number 20080312617, entitled "Disposable Absorbent Article with Substantially Continuous Distributed Absorbent Particulate Polymer Material and Method," filed on Dec. 18, 2008, which is hereby incorporated by reference, can be modified by removing the absorbent core, and modifying and/or replacing one or more of the remaining components of the article to make the article more robust and thus laundering resistant.

Alternatively, or in combination, the various component materials of laundering resistant outer covers may be combined using less labor intensive, but less durable, means, such as adhesive or mechanical or thermal bonds (e.g., vs. sewing). Further, the construction of a material, can affect the strength of the material and its ability to withstand degradation when subjected to wash cycles. For example, the type, strength, and degree of bonding in a material can affect the strength of the material, which may then affect whether or not the material is launderable or laundering resistant.

For outer covers that are laundering resistant, materials may include any natural or synthetic nonwoven web and/or film materials known in the diaper or pant arts. Laundering resistant materials of which an outer cover may be constructed may include non-woven web materials of polypropylene and/or polyethylene fibers, polyester fibers, and any other synthetic fibers used to form nonwoven web materials used as components of disposable diapers, and blends thereof. Natural fibers such as cotton, linen, wool, bamboo, hemp, silk, rayon, and the like may be blended with synthetic fibers to form such a nonwoven web suitable as a component layer of an outer cover. In addition to these materials, films, such as polyolefin films (microporous or non-microporous) can also be used in a laundering resistant outer cover.

Non-limiting examples of fibers, nonwovens and laminates of nonwovens and films that might be considered for use as laundering resistant outer cover materials may be found in U.S. Pat. Nos. 7,223,818; 7,211,531; 7,060,149; 6,964,720; 6,905,987; 6,890,872; 6,884,494; 6,878,647; and 5,518,801; and U.S. Published Applications Nos. 2008/0319407; 2008/0045917; 2007/0293111; 2007/0287983; 2007/0287348; 2007/0249254; 2007/0203301; and 2005/0164587.

Laundering resistant outer cover materials also may be selected to impart desired comfort, appearance and performance to the outer cover. In some circumstances it also may be desired to select laundering resistant outer cover materials which are sufficiently inexpensive to allow for disposal, if soiled extensively or damaged, with minimized issues of cost or conscience.

The outer cover also, or additionally, may include a laminated or substantially separate film layer, which may be elastic, to provide enhanced liquid penetration resistance and/or elastic properties. Elastic properties also can be added or enhanced via the addition of other materials to the outer cover in layer, band or strip fashion, including elastic strands, bands, scrims, foams, and the like. A film layer may be laminated with a launderable material or laundering resistant material. A film layer may include an elastomer based on KRATON (a product of Kraton Polymers U.S., LLC, Houston, Tex.); VISTAMAXX available from ExxonMobil Chemical Company, Houston, Tex.; FLEXAIRE, EXTRAFLEX or FABRIFLEX (products of Tredegar Film Products Corporation, Richmond, Va.), and various latex-free elastomeric sheets available from Fulflex Elastomerics Worldwide (Greenville, Tenn.).

Inclusion of an elastomeric material, either as a fibrous component of a cloth or nonwoven layer, or as a film layer, provides for improved stretchability and elasticity where it may be deemed useful to accommodate the wearer's anatomy and movements, such as over the wearer's buttocks and/or around the waist areas, and improved fit and comfort. Additionally, where a film layer may be included, it may impart additional liquid containment capability to the outer cover. A film layer may include a film that is substantially liquid impermeable, but vapor permeable, so as to provide breathability and reduce humidity within the outer cover while it is being worn, reducing chances for overhydration of the skin where liquid containment capability is desired.

Layers or elements of the outer cover may be joined to each other via any means known in the diaper or clothing art, including, for example, adhesives, mechanical bonding, ultrasonic bonding, sewing, stitching, serging, edging, and the like.

It is contemplated that any laundering resistant outer cover disclosed herein can be used with any embodiment of a wearable absorbent article disclosed herein. The exemplary laundering resistant outer cover can also be added for use in a pant type wearable absorbent article.

Reusable outer covers may need to be washed prior to reuse if they become soiled by bodily exudates, such as urine, feces, or sweat, or by environmental contaminants. Caregivers may also choose to wash the outer cover to freshen it, remove malodors, add a pleasant fragrance, or generally restore its shape, neatness, and/or appearance. In general, caregivers may expect more expensive outer covers to be washable a greater number of wash cycles without significant deterioration of physical properties or appearance of the outer cover. Laundering resistant outer covers may be generally constructed of less expensive materials than launderable outer covers and, therefore, expected to deteriorate more rapidly with increasing number of washing cycles, e.g., deteriorate beyond the point of usefulness after fewer washing cycles, than launderable outer covers.

While the aesthetic appearance of the outer cover after multiple wash cycles is important to some caregivers' perceived value of the outer cover, the acceptable appearance is highly dependent on individual preference. Also, even outer covers with a more "worn" appearance may be acceptable to wear in certain places (e.g., home) or usage situations (e.g., overnight or when child has an illness such as diarrhea). Therefore, it is more critical that laundering resistant outer covers and launderable outer covers be capable of their intended use after at least one wash cycle and 10 wash cycles, respectively.

The outer cover should retain significant dimensional stability after the intended minimum number of wash cycles. Since the dimensions of the outer cover significantly impact the size of the wearer the outer cover will fit comfortably, securely, and/or without gapping, it is desirable that the outer cover dimensions vary by less than about 10%, more preferably less than about, 5% over the outer cover's useful life. Some launderable outer covers may experience a significant one-time shrinkage from the first wash cycle (that is, the initial washing for an outer cover that was previously unwashed), in a manner similar to that inherently experienced by other durable wearable articles, such as clothing, constructed from textile and/or woven materials. In these cases, the article, or components thereof, may be pre-washed by the manufacturer or consumer to avoid any potential fit issues with the first usage cycle of the article. However, for launderable outer covers that do experience a significant one-time shrinkage from the first wash cycle, it is desirable that the outer cover dimensions vary by less than about 10%, more preferably less than about, 5% after the first-wash. Alternatively, launderable articles may be constructed of shrink-resistant materials. For laundering resistant articles, on the other hand, it is desirable for such articles to maintain dimensional stability after one wash cycle due to their intended shorter product lifespan.

After washing, the outer cover should also retain its ability to stretch, especially in waist region, in order to be able to accommodate a wider range of wearer sizes and/or movements. A given desired amount of extension, i.e., for size adjustment or comfortable freedom of movement, should be achieved at an applied stress within the range of typical forces applied to an article by a wearer. Despite the washing, the force required to achieve the desired extension, e.g., the Whole Product Back Extension Force, should remain relatively constant during the useful life of the article in order to maintain the same fit range and containment performance. If the Whole Product Back Extension Force at a given extension increases significantly with repeated wash cycles, the product size range may decrease and the product may become too tight, leading to skin marking. If the Whole Product Back Extension Force decreases significantly with repeated wash cycles, the product may fit too loosely, leading to sagging, gapping, and increased leakage of bodily exudates. The Whole Product Back Extension Force at a given extension should not vary by more than about 25%, and more preferably 10%, after repeated wash cycles during the intended lifespan of the article. As with dimensional stability, launderable outer covers may experience a change in properties greater than this after the first wash cycle, but then maintain such relatively stable Whole Product Back Extension forces thereafter.

Additionally, after washing, the outer cover should maintain tension in the waist region after the article is stretched and allowed to recover. If the Whole Product Back Extension unload force at a given extension decreases too much, the product may be at risk of significant sagging, gapping, and leakage due to insufficient sustained fit. The Whole Product Back Extension unload force at a given extension should not decrease by more than about 25%, and more preferably 10%, after repeated wash cycles during the intended lifespan of the article. The absolute Whole Product Back Extension unload force at 25% extension should remain greater than about 0.5N, preferably greater than about 0.75N and 1.0N, after repeated wash cycles during the intended lifespan of the article.

Further, despite being subjected to wash cycles, the elastic forces in a leg band of an outer cover should also remain relatively constant during the useful life of the article in order to maintain the same fit range and containment performance. If the elastic forces in a leg band increase significantly when the outer cover is subjected to wash cycles, then the product size range may decrease and the product may become too tight, leading to skin marking. If the elastic forces in a leg band decrease significantly when the outer cover is subjected to wash cycles, then the product may fit too loosely, leading to sagging, gapping, and increased leakage of bodily exudates. The elastic forces in a leg band at a given extension should not vary by more than about 25%, and more preferably 10%, after repeated wash cycles during the intended lifespan of the article. As with dimensional stability, launderable outer covers may experience a change in properties greater than this after the first wash cycle, but then maintain such relatively stable elastic forces in the leg band thereafter.

Three samples of the exemplary launderable outer cover and three samples of the exemplary laundering resistant outer cover described above were each evaluated both prior to washing and after one or more wash cycles. Several important dimensions were measured on these outer covers in a flat, laid-out orientation after various numbers of wash cycles, including: (1) an overall longitudinal length of the outer cover, measured along the longitudinal centerline, from one end of the outer cover to the other (2) an overall lateral width of the back waist region of the outer cover, measured across the widest portion of the back waist region between the laterally most outboard points on the ears, and (3) a lateral width between the farthest laterally inboard points along the edges of the fastening elements on the back ears of the outer cover. All of these dimensions were measured according to the measurement guidelines described herein. Additionally, elastic forces in the elastic leg band of the outer cover were measured at 85% extension, according to the test method described herein. Finally, the Whole Product Back Extension Force was measured across the back of the outer cover, from a first point on one fastening element to a second point located laterally across from the first point and on the other fastening element, at 25% strain (first extension cycle), according to the test method described herein. The data from this testing are presented in the table below, as averages of the three samples.

dering resistant outer cover decreased by 50% or more after 5 to 10 wash cycles to levels significantly lower than 1.0 N, while the Whole Product Back Extension unload force for the exemplary launderable outer cover remained relatively constant after the first wash initial shrinkage, and above 1.0N.

In a wash cycle, a component of an absorbent article, such as an outer cover, is machine washed and machine dried

TABLE 1

| Property | unwashed (0 wash cycles) | after 1 wash cycle | after 2 wash cycles | after 3 wash cycles | after 4 wash cycles | after 5 wash cycles | after 10 wash cycles |
|---|---|---|---|---|---|---|---|
| Dimensions (mm) Exemplary laundering resistant outer cover | | | | | | | |
| Lateral width between fasteners | 260 | 259 | | | | 231 | 232 |
| Overall lateral width of back waist region | 310 | 310 | | | | 280 | 282 |
| Overall longitudinal length | 340 | 337 | | | | 315 | 315 |
| Exemplary launderable outer cover | | | | | | | |
| Lateral width between fasteners | 280 | 265 | 258 | 260 | 262 | 263 | 262 |
| Overall lateral width of back waist region | 335 | 318 | 308 | 312 | 298 | 313 | 308 |
| Overall longitudinal length | 305 | 283 | 293 | 288 | 292 | 282 | 280 |
| Leg Force (N) at 85% strain | | | | | | | |
| Exemplary laundering resistant outer cover | 1.19 | | | | | 1.95 | 1.97 |
| Exemplary launderable outer cover | 2.76 | 2.28 | 2.60 | 2.81 | 3.03 | 3.01 | 2.76 |
| Whole product back extension forces (N) Exemplary laundering resistant outer cover | | | | | | | |
| 25% strain $1^{st}$ load | 2.34 | 3.00 | | | | 1.80 | 1.64 |
| 25% strain $1^{st}$ unload | 1.01 | 1.48 | | | | 0.59 | 0.50 |
| Exemplary launderable outer cover | | | | | | | |
| 25% strain $1^{st}$ load | 3.88 | 2.72 | 2.63 | 2.75 | 2.87 | 2.78 | 2.98 |
| 25% strain $1^{st}$ unload | 2.07 | 1.15 | 1.20 | 1.14 | 1.16 | 1.18 | 1.13 |

As shown in Table 1, the dimensions of the exemplary laundering resistant outer cover remained relatively unchanged, and still useful, after one wash cycle, but degraded about 10% after 5 or 10 wash cycles. On the other hand, the dimensions of the exemplary launderable outer cover experienced a one-time shrinkage of 5 to 7% after one wash cycle, but then remained relatively constant through at least 10 wash cycles.

As shown in Table 1, the Leg Force at 85% strain for the exemplary laundering resistant outer cover increased by 60-70% after 5 wash cycles. The Leg Force at 85% strain for the exemplary launderable outer cover remained relatively constant over the first 10 wash cycles.

As shown in Table 1, the Whole Product Back Extension forces at 25% strain ($1^{st}$ load and first unload) for the exemplary laundering resistant outer cover experienced significant degradation after 5 wash cycles. The Whole Product Back Extension forces at 25% strain ($1^{st}$ load and first unload) for the exemplary launderable outer cover remained relatively constant after the first wash initial shrinkage. The Whole Product Back Extension unload force for the exemplary launaccording to the protocol from AATCC (American Association of Textile Chemists and Colorists) Test Method 124-2001, with the selected parameters and variations listed below.

AATCC Test Method 124-2001 a) Per section 6, Apparatus and materials, a Kenmore 600 (Heavy Duty—Super Capacity Plus—Quiet Pak) is used for the automatic washing machine, and a Maytag Commercial (such as model numbers MDE27MNACW, MDE15MNAYW, and MDE13MNACW) is used for the automatic tumble dryer.

b) Despite the instructions in Section 6, Apparatus and materials, the following ballast is used: Test Fabric style 493 from Testfabrics, Inc, West Pittston, Pa., which is cotton sheeting, with a thread count of 60×60, a weight of 151 gsm, and a size of 55' by 39".

c) Despite the instructions in Section 6, Apparatus and materials, the evaluation area is not configured according to section 6.7 and the apparatus of section 6.8 is not used. Instead, all visual evaluations are perfomed under typical artificial lighting conditions (e.g. fluorescent light), which allows a person with normal vision to clearly see.

d) Despite the instructions in Section 7, Test Specimen, the component to be tested is (as necessary) entirely removed from the rest of the absorbent article, and (to the extent allowed by the removal) the component is tested as an undamaged whole. Up to three components of the same type are washed simultaneously.

e) Regarding the machine wash in Section 8.2.2, use the "large" setting on the machine for the water level, select a wash temperature of 32+/−3° C. (90+/−5° F.), and a rinse temperature of 16+/−3° C. (60+/−5° F.).

f) Regarding the settings in Section 8.2.2, select Normal/Cotton Sturdy, which has a washing time of 12 minutes, an initial spin time of 6 minutes, a refill time of 4 minutes, a rinse time of 5 minutes, and a final spin cycle time of 6 minutes.

g) Regarding the Drying in Section 8.3, select Cotton Sturdy and Whites & Colors.

h) Despite the instructions in Section 8.5, the steps of conditioning and preconditioning are not performed.

i) Despite the instructions in Section 9, Evaluation, these evaluation steps are not performed. Instead, the tested component is evaluated by one of skill in the art, to determine whether the testing has resulted in significant degradation to the appearance or performance of the article that would render it unsuitable for its intended functionality and/or use.

Measurement Guidelines

To measure an overall lateral width of a back waist region of an outer cover: 1) lay the outer cover flat on a horizontal surface with the inside facing up, 2) lay a calibrated ruler on top of the outer cover, in the back waist region, with the ruler oriented parallel to the lateral centerline of the outer cover (do so without stretching or smoothing the outer cover), 3) measure the overall linear distance parallel to the lateral centerline from the farthest laterally outboard point on one side of the outer cover to the farthest laterally outboard point on the other side of the outer cover, 4) record the measurement to the nearest millimeter.

To measure a lateral width between fasteners of an outer cover: 1) lay the outer cover flat on a horizontal surface with the inside facing up, 2) lay a calibrated ruler on top of the outer cover, in the back waist region, with the ruler oriented parallel to the lateral centerline of the outer cover (do so without stretching or smoothing the outer cover), 3) measure the overall linear distance parallel to the lateral centerline from the farthest laterally inboard point of a fastener on one side of the outer cover to the farthest laterally inboard point of a fastener on the other side of the outer cover, 4) record the measurement to the nearest millimeter.

Test Method for Determining Whole Product Back Extension Forces

Whole product back extension forces are measured on a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. Both the movable (upper) and stationary (lower) pneumatic jaws are fitted with 1 inch×1 inch diamond faced grips.

Program the tensile tester to extend the specimen to 200% strain at a rate of 254 mm/min, hold at that strain for 30 sec. and then return to 0% strain at 254 mm/min. After 60 sec. again extend the sample to 200% strain at 254 mm/min., hold for 30 sec. and then return to 0% strain at 254 mm/min. Set the data acquisition rate to 100 Hz. From the force versus % strain curve, program the software to report the force (N) at 25% strain on the first load cycle, and at 25% strain on the first unload cycle.

Set the gage length to the length 195 as shown in FIG. 1. Zero the crosshead. Insert the specimen into the upper grips, aligning the edge of the fasteners 154 that is proximal to 113 with the lower edge of the grip face and close the grips. Zero the load cell. Insert the other end of the specimen into the lower grips aligning the edge of the fasteners 154 that is proximal to 113 with the upper edge of the grip face, and close the grips. The specimen should be under enough tension to eliminate any slack in the sample. Start the tensile tester's program, and record data.

Report the force (N) at 25% strain on the first load cycle, and at Force (N) at 25% strain on the first unload cycle to ±0.01 N.

Test Method for Determining Leg Force at 85% Extension

The leg force at 85% extension is measured on a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell (typically 10N). Both the movable (upper) and stationary (lower) pneumatic jaws are fitted with 1 inch×1 inch rubber faced grips. The gage length is set as 100 mm, and the data acquisition rate is set to 100 Hz.

Locate the two terminal ends of the leg elastic in the outer cover; that is the locations where the elastic is secured by adhesive, sewing or other means. Using a felt tipped marker, draw a line at each end. Extend the leg cuff to its full extension and measure its extended length between the two marks to the nearest 1 mm. Record this length as the cuff length. Calculate the extensions as follows:

$$95\% \text{ extension (mm)} = (\text{cuff length} \times 0.95) - \text{gage length}$$

$$85\% \text{ extension (mm)} = (\text{cuff length} \times 0.85) - \text{gage length}$$

Program the tensile tester to extend the specimen to 95% extension at 254 mm/min., hold at this extension for 5 sec., and return at a rate of 254 mm/min to the original crosshead position. Hold for an additional 5 sec. and again extend to 95% extension at 254 mm/min., hold at this extension for 5 sec. and return at a rate of 254 mm/min to original crosshead position. From the force (N) verses extension curve (mm), program the software to report the force at 85% extension on the second return cycle.

Set the gage length to 100 mm and zero the crosshead. Insert one end of the leg cuff into the top grip, aligning the bottom edge of the grip face with the mark at one of the ends, and close the grip face. Zero the load cell. Insert the other end of the leg cuff into the bottom grip, aligning the top edge of the grip face with the mark at the other end, and close the grip face. Start the tensile tester's program and collect data.

Report the force (N) at 85% extension from the second unload cycle to ±0.01 N.

Embodiments of the present disclosure include reusable outer covers that perform well after being laundered. The designs of these outer covers help prevent wearable absorbent articles from sagging or slipping down on a wearer. As a result, wearable absorbent articles with the reusable outer covers of the present disclosure can feel comfortable, look attractive, and perform well as the articles tend to stay in place on wearers and not leak.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable absorbent article comprising:
   a reusable outer cover configured to cover an absorbent core and to form an outside of a wearable absorbent article, including an elastic leg band, wherein in an unwashed condition the elastic leg band has a first particular leg force and, after at least one wash cycle the elastic leg band has a second particular leg force that is equal to the first particular leg force +/−20%; and
   a disposable absorbent core.

2. The reusable outer cover of claim 1, wherein the outer cover is launderable.

3. The reusable outer cover of claim 1, wherein the outer cover is laundering resistant.

4. The reusable outer cover of claim 1, wherein after at least five wash cycles the elastic leg band has a second particular leg force that is equal to the first particular leg force +/−20%.

5. The reusable outer cover of claim 1, wherein after at least ten wash cycles the elastic leg band has a second particular leg force that is equal to the first particular leg force +/−20%.

6. A wearable absorbent article comprising:
   a reusable outer cover configured to cover an absorbent core and to form an outside of a wearable absorbent article, wherein in an unwashed condition the outer cover has a whole product back extension first particular force and, after at least one wash cycle has a whole product back extension second particular force that is equal to the first particular force +/−20%; and
   a disposable absorbent core.

7. The reusable outer cover of claim 6, wherein the outer cover is launderable.

8. The reusable outer cover of claim 6, wherein the outer cover is laundering resistant.

9. The reusable outer cover of claim 6, wherein the first particular force is a load force strain.

10. The reusable outer cover of claim 6, wherein the first particular force is an unload force.

11. The reusable outer cover of claim 6, which after at least five wash cycles has a whole product back extension second particular force that is equal to the first particular force +/−20%.

12. The reusable outer cover of claim 6, which after at least ten wash cycles has a whole product back extension second particular force that is equal to the first particular force +/−20%.

13. A reusable outer cover configured to cover an absorbent core and to form an outside of a wearable absorbent article, wherein the outer cover experiences a dimensional shrinkage that is less than or equal to about 20% after at least one wash cycle, and wherein the reusable outer cover comprises fastening elements for the absorbent core.

14. The reusable outer cover of claim 13, wherein the fastening elements are patches of loops.

15. The reusable outer cover of claim 13, wherein the outer cover experiences a first dimensional shrinkage with a first wash cycle, and experiences a subsequent dimensional shrinkage that is less than or equal to about 20% for a wash cycle subsequent to the first wash cycle.

16. The reusable outer cover of claim 13, wherein the outer cover experiences a first dimensional shrinkage that is less than or equal to about 20% for a first wash cycle.

17. The reusable outer cover of claim 13, wherein the outer cover is launderable.

18. The reusable outer cover of claim 13, wherein the outer cover is laundering resistant.

19. The reusable outer cover of claim 13, wherein the outer cover experiences a dimensional shrinkage that is less than or equal to about 5% after at least one wash cycle.

20. The reusable outer cover of claim 13, wherein the outer cover experiences a dimensional shrinkage that is less than or equal to about 10% after at least one wash cycle.

21. The reusable outer cover of claim 20, wherein the outer cover experiences a first dimensional shrinkage with a first wash cycle, and experiences a subsequent dimensional shrinkage that is less than or equal to about 10% for a wash cycle subsequent to the first wash cycle.

22. The reusable outer cover of claim 20, wherein the outer cover experiences a first dimensional shrinkage that is less than or equal to about 10% for a first wash cycle.

23. The reusable outer cover of claim 22, wherein the outer cover experiences a subsequent dimensional shrinkage that is less than or equal to about 20% for a wash cycle subsequent to the first wash cycle.

24. The reusable outer cover of claim 22, wherein the outer cover experiences a subsequent dimensional shrinkage that is less than or equal to about 20% after at least five wash cycles.

25. The reusable outer cover of claim 20, including a first side ear with a first fastener, a second side ear with a second fastener, and a lateral width between the fasteners, wherein the lateral width experiences a dimensional shrinkage that is less than or equal to about 10% after at least one wash cycle.

26. The reusable outer cover of claim 20, including a back waist with an overall lateral width, wherein the overall lateral width experiences a dimensional shrinkage that is less than or equal to about 10% after at least one wash cycle.

27. The reusable outer cover of claim 20, including an overall longitudinal length, wherein the overall longitudinal length experiences a dimensional shrinkage that is less than or equal to about 10% after one wash cycle.

28. The reusable outer cover of claim 20, wherein substantially all of the reusable outer cover is formed from a nonwoven fabric.

29. The reusable outer cover of claim 20, wherein the dimensional shrinkage is less than or equal to about 10% after at least five wash cycles.

30. The reusable outer cover of claim 20, wherein the dimensional shrinkage is less than or equal to about 10% after at least ten wash cycles.

31. A wearable absorbent article comprising the reusable outer cover of claim 20 and a disposable absorbent core.

* * * * *